(12) United States Patent
DeGeorge et al.

(10) Patent No.: US 8,088,176 B2
(45) Date of Patent: Jan. 3, 2012

(54) METHODS AND KITS FOR PERMANENTLY COLORING HAIR USING A DEVELOPER COMPOSITION CONTAINING AN OXIDIZER COMPOSITION AND A SHAMPOO

(75) Inventors: Michael DeGeorge, Middletown, NJ (US); Jeremy Puco, Budd Lake, NJ (US); Delphine Allard, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/060,937

(22) PCT Filed: Aug. 28, 2009

(86) PCT No.: PCT/IB2009/007003
§ 371 (c)(1),
(2), (4) Date: May 6, 2011

(87) PCT Pub. No.: WO2010/023559
PCT Pub. Date: Mar. 4, 2010

(65) Prior Publication Data
US 2011/0209720 A1    Sep. 1, 2011

Related U.S. Application Data

(60) Provisional application No. 61/092,768, filed on Aug. 29, 2008.

(51) Int. Cl.
*A61Q 5/10* (2006.01)
(52) U.S. Cl. ......... 8/405; 8/406; 8/410; 8/426; 132/202; 132/208

(58) Field of Classification Search .............. 8/405, 406, 8/410, 426; 132/202, 208
See application file for complete search history.

(56) References Cited

U.S. PATENT DOCUMENTS

| 5,560,750 | A | 10/1996 | Crews et al. |
| 2003/0140428 | A1 | 7/2003 | Patel et al. |
| 2005/0097684 | A1 | 5/2005 | Narasimhan et al. |

FOREIGN PATENT DOCUMENTS

| EP | 0146350 A2 | 6/1985 |
| GB | 200375 A | 7/1923 |
| JP | 3 258714 A | 11/1991 |
| JP | 2002 137916 A | 5/2002 |
| WO | WO-2007/096409 A1 | 8/2007 |
| WO | WO 2009/010883 A2 * | 1/2009 |
| WO | WO-2009/010883 A2 | 1/2009 |

* cited by examiner

*Primary Examiner* — Eisa Elhilo
(74) *Attorney, Agent, or Firm* — Connolly Bove Lodge & Hutz LLP

(57) ABSTRACT

Disclosed are methods, kits and compositions for coloring the hair involving a color base composition having: at least one oxidation dye precursor, and at least 5% by weight water based on the weight of the color base composition, wherein the color base composition has a pH ranging from 2 to 12; and a developer composition made from a combination of an anhydrous oxidizer composition containing at least one oxidizing agent chosen from persulfates, perborates, percarbonates, their salts, and mixtures thereof, and a shampoo composition containing a carrier vehicle and at least 4% of at least one surfactant.

20 Claims, No Drawings

METHODS AND KITS FOR PERMANENTLY COLORING HAIR USING A DEVELOPER COMPOSITION CONTAINING AN OXIDIZER COMPOSITION AND A SHAMPOO

CROSS REFERENCE TO RELATED APPLICATIONS

This application is a National Phase filing under 35 U.S.C. §371 of PCT/IB2009/007003 filed on Aug. 28, 2009; and this application claims priority to U.S. Provisional Application No. 61/092,768 filed on Aug. 29, 2008 under 35 U.S.C. §119; the entire contents of all are hereby incorporated by reference.

BACKGROUND OF THE INVENTION

Imparting a color change or color effect on hair can be done using permanent and semi-permanent or temporary hair coloring products. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents. Such permanent hair color products also contain ammonia or other alkalizing agents such as monoethanolamine (MEA) which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

It is also known that it is possible to vary the shades obtained with the primary intermediates by combining them with couplers or coloration modifiers. The variety of molecules used as primary intermediates and couplers can allow a wide range of colors to be obtained.

The artificial color of hair treated with a permanent hair coloring product does not easily wash out during the course of routine shampooing. The colorations obtained show good longevity (also referred to as color-fastness) with exposure to shampoo.

It has been surprisingly found that by employing a method of coloring keratinous substrates involving the steps of applying a color base composition containing at least one primary dye intermediate onto the hair, followed by application of a developer composition formed from the combination of an anhydrous oxidizer composition containing at least one oxidizing agent chosen from persulfates, perborates, percarbonates, and salts thereof, and a shampoo composition in a carrier vehicle onto the hair, either immediately after, or at any time thereafter that is convenient to the consumer from the time of application of the color base composition, for example up to 60 minutes thereafter, the following several significant advantages can be realized, as compared to the use of conventional permanent dyeing techniques: shorter dyeing time; comparable color-fastness to conventional permanent hair dyeing methods using peroxide developers; improved color deposit on the hair; little to no odor. In some instances, depending on the oxidative dye and/or coupler molecule used, different colors/shades may be obtained compared to the conventional hair coloring compositions/methods using peroxide developers.

Another disadvantage associated with the use of conventional permanent hair dye formulations and systems is that they are very messy to apply and have a tendency to cause scalp staining.

Thus, it is also an object of the present invention to provide a means of permanently coloring hair in a less messy or cleaner manner and to provide a novel and convenient means of coloring hair wherein the at least one oxidizing agent is delivered in a shampoo system to the hair treated with the color base composition Another object of the invention is to provide a permanent hair coloring system that does not lift the color of the hair, that is, it does not lighten hair color but is still able to vary the tone of the hair color or make the hair color darker. Lifting is defined as the process by which the natural hair melanin is removed, thereby leaving the hair lightened from its natural color.

In oxidative coloration processes, the alkaline environment ensures that the cuticles of the hair are opened to allow penetration of an oxidizing agent, such as hydrogen peroxide. Such an oxidizing agent breaks down the melanin by providing it with oxygen, and the melanin molecule is colorless when oxidized.

Another object of the present invention is to provide a means of permanently coloring hair in the absence of a peroxide raw material ingredient.

BRIEF SUMMARY OF THE INVENTION

The present invention is directed to a method of permanently coloring hair involving the steps of:
(a) providing a color base composition containing:
  (i) at least one primary dye intermediate chosen from ortho-aminophenols, para-aminophenols, ortho-phenylenediamines, para-phenylenediamines, double bases, heterocyclic bases, the acid addition salts thereof, and mixtures thereof; and
  (ii) at least 5% by weight of water, based on the total weight of the color base composition, wherein the color base composition has a pH ranging from 2 to 12;
(b) applying the color base composition onto the hair;
(c) rinsing the color base composition from the hair;
(d) providing an anhydrous oxidizer composition containing at least one oxidizing agent chosen from persulfates, perborates, percarbonates, their salts, and mixtures thereof;
(e) providing a shampoo composition containing a carrier vehicle and at least 4% by weight, based on the total weight of the shampoo composition, of at least one surfactant chosen from anionic, amphoteric, nonionic, zwitterionic, cationic surfactants, and mixtures thereof;
(f) combining (d) and (e), immediately prior to use, to form a developer composition, wherein the developer composition contains from 1% to 80% by weight of the oxidizing agent, based on the total weight of the developer composition;
(g) applying the developer composition onto the hair in order to develop color, in situ, to form colored hair; and
(h) rinsing the developer composition from the hair.

According to a preferred embodiment, the color base composition and the developer composition are each substantially free of any oxidation catalyst.

Similarly, according to a preferred embodiment, the color base composition and the developer composition are each free of peroxide.

The present invention is also directed to a kit for permanently coloring hair, the kit containing:
(a) a multi-unit receptacle;

(b) at least one unit comprising a color base composition, the color base composition containing:
  (i) at least one primary dye intermediate chosen from ortho-aminophenols, para-aminophenols, ortho-phenylenediamines, para-phenylenediamines, double bases, heterocyclic bases, the acid addition salts thereof, and mixtures thereof; and
  (ii) at least 5% by weight of water, based on the total weight of the color base composition, wherein the color base composition has a pH ranging from 2 to 12; and
(c) at least one unit comprising an anhydrous oxidizer composition containing at least one oxidizing agent chosen from persulfates, perborates, percarbonates, their salts, and mixtures thereof; and
(d) at least one unit comprising a shampoo composition containing a carrier vehicle and at least 4% by weight, based on the total weight of the shampoo composition, of at least one surfactant chosen from anionic, amphoteric, nonionic, zwitterionic, cationic surfactants, and mixtures thereof.

Here too, according to a preferred embodiment, the color base composition, the oxidizer composition and the shampoo composition are all substantially free of any oxidation catalyst.

Similarly, according to a preferred embodiment, the color base composition, the oxidizer composition, and the shampoo composition are all free of peroxide.

It should be noted that the description hereunder of the different embodiment of the invention applies for the method, as well as for the kit, of the present invention.

It should be further noted that by varying the pH of the system, different levels of color vibrancy can be achieved.

DETAILED DESCRIPTION OF THE INVENTION

Other than in the operating examples, or where otherwise indicated, all numbers expressing quantities of ingredients or reaction conditions are to be understood as being modified in all instances by the term "about".

As used herein, the expression "at least one" means one or more and thus includes individual components as well as mixtures/combinations.

As used herein, the term "applying" means contacting the hair to be dyed with the dye composition or with at least one of the compositions of the invention.

As used herein, "cosmetically acceptable" means that the item in question is compatible with any human keratin material and in particular human keratinous fibers, such as human hair.

As used herein, "conditioning" means imparting to at least one keratinous fiber at least one property chosen from combability, manageability, moisture-retentivity, luster, shine, and softness. In case of combing, the level of conditioning is evaluated by measuring, and comparing, the ease of combability of the treated hair and of the untreated hair in terms of combing work (gm-in).

As used herein, "formed from," means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

As used herein, the term "rheology modifier" means any compound capable of giving a viscosity to the oxidizing composition such that, once it is applied onto keratin fibres, this composition does not run, and remains perfectly localized at the point of application.

1. Color Base Composition

The present invention involves the use of a color base composition, containing at least one primary dye intermediate.

In this invention, the color base composition may contain a wide variety of oxidation dye precursors. These include one or more primary dye intermediates and, optionally, one or more couplers.

A. Primary Dye Intermediates

Suitable primary dye intermediates are well known for use in hair color, and include ortho or para aminophenols, ortho or para phenylenediamines, double bases, heterocyclic bases, and the acid addition salts thereof.

The para-phenylenediamines which can be used as primary dye intermediates in the color base composition of the invention can be chosen in particular from the compounds of the following formula (I) and their addition salts with an acid:

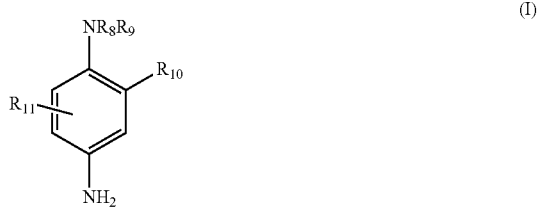

(I)

in which:

$R_8$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical, a $C_1$-$C_4$ alkyl radical substituted by a nitrogenous group, a phenyl radical or a 4'-aminophenyl radical;

$R_9$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical or a $C_1$-$C_4$ radical substituted by a nitrogenous group;

$R_8$ and $R_9$ can also form, with the nitrogen atom which carries them, a 5- or 6-membered nitrogenous heterocycle optionally substituted by one or more alkyl, hydroxyl or ureido groups;

$R_{10}$ represents a hydrogen atom, a halogen atom, such as a chlorine atom, a $C_1$-$C_4$ alkyl radical, a sulpho radical, a carboxyl radical, a $C_1$-$C_4$ monohydroxyalkyl radical, a $C_1$-$C_4$ hydroxyalkoxy radical, a $C_1$-$C_4$ acetylaminoalkoxy radical, a $C_1$-$C_4$ mesylaminoalkoxy radical or $C_1$-$C_4$ carbamoylaminoalkoxy radicals;

$R_{11}$ represents a hydrogen atom, a halogen atom or a $C_1$-$C_4$ alkyl radical.

Mention may in particular be made, among the nitrogenous groups in the above formula (I), of the amino, mono($C_1$-$C_4$) alkylamino, di ($C_1$-$C_4$) alkylamino, tri($C_1$-$C_4$)alkylamino, monohydroxy($C_1$-$C_4$) alkylamino, imidazolinium and ammonium radicals.

Mention may more particularly be made, among the, para-phenylenediamines of above formula (I), of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-β-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-((β-hydroxyethyloxy)-para-phenylenediamine, 2-((β-acetylaminoethyloxy)-para-phenylenediamine, N-(β-methoxyethyl)-para-phenylenediamine, 2-methyl-1-N-(β-hydroxyethyl)-para-phenylenediamine and their addition salts with an acid.

Preference is very particularly given, among the para-phenylenediamines of above formula (I), to para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and their addition salts with an acid.

Among the ortho-phenylenediamines, mention may be made of N1-(2-hydroxyethyl)-4-nitro-o-phenylenediamine, 4-methyl-o-phenylenediamine, and 4-nitro-o-phenylenediamine and acid addition salts thereof.

As used herein, the term double bases means compounds comprising at least two aromatic nuclei having at least one of amino and hydroxyl groups.

Mention may in particular be made, among the double bases which can be used as primary dye intermediates in the color base composition in accordance with the invention, of the compounds corresponding to the following formula (II) and their addition salts with an acid:

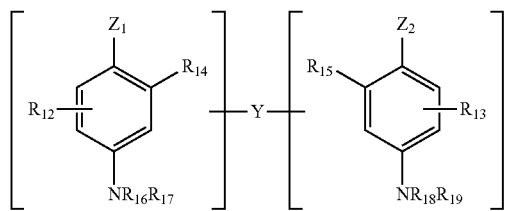

(II)

in which:
Z$_1$ and Z$_2$, which are identical or different, represent a hydroxyl or —NH$_2$ radical which can be substituted by a C$_1$-C$_4$ alkyl radical or by a connecting arm Y;
the connecting arm Y represents a linear or branched alkylene chain comprising from 1 to 14 carbon atoms which can be interrupted or terminated by one or more nitrogenous groups and/or by one or more heteroatoms, such as oxygen, sulphur or nitrogen atoms, and which is optionally substituted by one or more hydroxyl or C$_1$-C$_6$ alkoxy radicals;
R$_{12}$ and R$_{13}$ represent a hydrogen or halogen atom, a C$_1$-C$_4$ alkyl radical, a C$_1$-C$_4$ monohydroxyalkyl radical, a C$_2$-C$_4$ polyhydroxyalkyl radical, a C$_1$-C$_4$ aminoalkyl radical or a connecting arm Y;
R$_{14}$, R$_{15}$, R$_{16}$, R$_{17}$, R$_{18}$ and R$_{19}$, which are identical or different, represent a hydrogen atom, a connecting arm Y or a C$_1$-C$_4$ alkyl radical;
it being understood that the compounds of formula (II) only comprise a single connecting arm Y per molecule. Mention may in particular be made, among the nitrogenous groups of the above formula (II), of the amino, mono (C$_1$-C$_4$) alkylamino, di (C$_1$-C$_4$) alkylamino, tri(C$_1$-C$_4$)alkylamino, monohydroxy(C$_1$-C$_4$)alkylamino, imidazolinium and ammonium radicals.

Mention may more particularly be made, among the double bases of above formula (II), of N,N'-bis(β-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis(β-aminophenyl)-tetramethylenediamine, N,N'-bis(4-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine, 1,8-bis(2,5-diaminophenoxy)-3,5-dioxaoctane and their addition salts with an acid.

N,N'-Bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred among these double bases of formula (II).

The para-aminophenols which can be used in the context of the invention can be chosen in particular from the compounds corresponding to the following formula (III) and their addition salts with an acid:

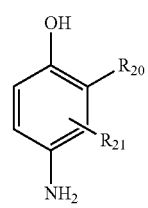

(III)

in which:
R$_{20}$ represents a hydrogen atom, a halogen atom, such as fluorine, a C$_1$-C$_4$ alkyl radical, a C$_1$-C$_4$ monohydroxyalkyl radical, a (C$_1$-C$_4$)alkoxy(C$_1$-C$_4$) alkyl radical, a C$_1$-C$_4$ aminoalkyl radical or a hydroxy(C$_1$-C$_4$)alkylamino-(C$_1$-C$_4$)alkyl radical,
R$_{21}$ represents a hydrogen atom, a halogen atom, such as fluorine, a C$_1$-C$_4$ alkyl radical, a C$_1$-C$_4$ monohydroxyalkyl radical, a C$_2$-C$_4$ polyhydroxyalkyl radical, a C$_1$-C$_4$ aminoalkyl radical, a C$_1$-C$_4$ cyanoalkyl radical or a (C$_1$-C$_4$) alkoxy(C$_1$-C$_4$) alkyl radical.

Among the preferred para-aminophenols, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, N-methyl-para-aminophenol, and the acid addition salts thereof.

The ortho-aminophenols that may be used as primary dye intermediates in the context of the present invention may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Among the heterocyclic bases that can be used as primary dye intermediates in the color base composition of the present invention, mention may be made of pyridine derivatives, pyrimidine derivatives, pyrazole derivatives, pyrazolinone derivatives, and the acid addition salts thereof.

Among the pyridine derivatives, mention may be made of the compounds described, for example, in patents GB 1,026, 978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6 methoxypyridine, 3,4-diaminopyridine, and the acid addition salts thereof.

Among the pyrimidine derivatives, mention may be made of the compounds disclosed, for example, in German Patent DE 2 359 399 or Japanese Patents JP 88-169 571 and JP 91-10659 or Patent Application WO 96/15765, such as 2,4, 5,6-tetra-aminopyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-triaminopyrimidine, and the pyrazolopyrimidine derivatives, such as those mentioned in French Application FR-A-2 750 048 and among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethyl-pyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-(imidazolylpropylamino)pyrazolo[1,5-a]pyrimidine; and their addition salts and their tautomeric forms, when there exists a tautomeric equilibrium, and their addition salts with an acid.

Among the pyrazole and pyrazolinone derivatives, mention may be made the compounds described in patents DE 3,843,892, DE 4,133,957 and patent applications WO 94/08969, WO 94/08970, FR-A-2,733,749, and DE 195 43 988, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(p-hydroxyethyl)amino-1-methylpyrazole, 2-(4,5-diamino-1H-pyrazol-1-yl), $H_2SO_4$, 2,3-diamino-6,7-dihydro-1H,5H-pyrazolo[1,2-z]pyrazol-1-one, 1-methyl-3-phenyl-2-pyrazolinone, and the acid addition salts thereof.

Preferred primary dye intermediates are p-phenylenediamine, p-aminophenol, o-aminophenol, N,N-bis(p-hydroxyethyl)-p-phenylenediamine, 2,5-diaminotoluene, their salts and mixtures thereof.

The primary dye intermediates may be employed in amounts ranging from 0.0001% to 12% by weight, preferably from 0.0001% to 8.0% by weight, more preferably, from 0.005% to 5% by weight, based on the total weight of the color base composition.

B. Color Couplers

The color base composition of the present invention may also contain one or more coupler compounds. The couplers that may be used in the dyeing method disclosed herein include those conventionally used in oxidation dye compositions, that is to say, meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and the acid addition salts thereof.

Suitable color couplers include, for example, those having the general formula (IV):

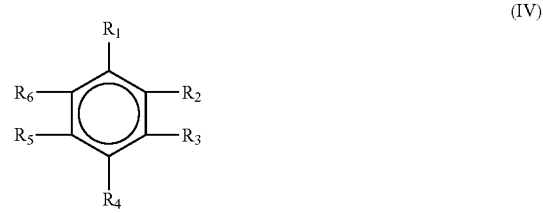

(IV)

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Other couplers may be chosen, for example, from 2,4-diamino-1-(β-hydroxyethyloxy)benzene, 2-methyl-5-aminophenol, 5-N-(β-hydroxyethyl) amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, 6-methyl pyrazolo [1,5-a]-benzimidazole, and the acid addition salts thereof.

Preferred couplers include resorcinol, 1-naphthol, 2-methylresorcinol, 4-amino-2-hydroxy toluene, m-aminophenol, 2,4-diaminophenoxyethanol, phenyl methyl pyrazolone, hydroxybenzomorpholine, 2-methyl-5-hydroxyetyylaminophenol, 6-hydroxyindole, 2-amino-3-hydroxypyridine, 5-amino-6-chloro-o-cresol, 4-chlororesorcinol, their salts, and mixtures thereof.

When they are present, these couplers may be present in amounts ranging from 0.0001% to 12% by weight; preferably from 0.001% to 8% by weight, based on the total weight of the color base composition.

In general, the acid addition salts of the oxidation bases and couplers may be chosen from hydrochlorides, hydrobromides, sulphates, tartrates, lactates, and acetates.

C. Cosmetically Acceptable Medium

The color base composition of the invention is formulated in a cosmetically acceptable medium, comprising water, and, optionally organic solvents.

The color base composition of the present invention comprises at least 5% by weight, preferably at least 20% by weight, and even more preferably at least 30% by weight of water, based on the total weight of said color base composition.

According to a preferred embodiment, the color base composition comprises water and at least one co-solvent chosen from organic solvents.

Suitable organic solvents include alcohols, such as ethanol, isopropyl alcohol, benzyl alcohol and phenyl ethyl alcohol; glycols and glycol ethers, such as ethylene glycol, propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, polybutene, hydrogenated polyisobutene, hydrogenated polydecene, polydecene, squalene, petrolatum and isoparaffins; and mixtures, thereof.

The at least one co-solvent may be present in an amount ranging from 1% to 30% by weight, such as from 2% to 20% by weight, relative to the total weight of the color base composition.

The color base composition of the present invention has a pH ranging from 2 to 12, and can be acidic, or alkaline.

Therefore, according to a first embodiment of the present invention, the color base composition has a pH ranging from 2 to 6.9, more preferably from 3 to 6.9, and even more preferably from 4.5 to 6.9.

According to a second embodiment of the present invention, the color base composition has a pH ranging from 7 to 12, more preferably from 8 to 11, and even more preferably from 9 to 10.

If necessary, suitable pH adjusters may be used to obtain the above-disclosed pH values. Examples of suitable pH adjusters include, but are not limited to, monoethanolamine, ammonium hydroxide, sodium hydroxide, arginine, aminomethyl propanol.

D. Other Optional Ingredients of the Color Base Composition

The color base composition of the invention can also optionally contain other types of colorants. Suitable hair colorants include, but are not limited to, pigments, liposoluble dyes, direct dyes, nacreous pigments, pearling agents, leuco dyes, optical lightening colorants, natural colorants and optically-variable pigments.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, DC Blue No. 14, annatto, and quinoline yellow. The liposoluble dyes, when present, may have a concentration ranging up to 20% by weight of the total weight of the color base composition, such as from 0.0001% to 6% by weight.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the color base composition in a concentration ranging up to 50% by weight of the total weight of the color base composition, such as from 0.1% to 20% by weight, preferably from 0.1% to 15% by weight.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, silica, ferric blue, and mixtures thereof. Representative examples of organic pigments include carbon black, pigments of D & C type, and lakes based on cochineal carmine, barium, strontium, calcium, and aluminum. Other examples of pigments are ultramarines, HC Blue No. 14, Ext. Yellow 7, Yellow 10 Lake, and acid violet 43.

If present, the pigments may be present in the composition in a concentration ranging up to 50% by weight of the total weight of the color base composition, such as from 0.5% to 40% by weight, and further such as from 2% to 30% by weight.

A direct dye is a colored substance that does not require the use of an oxidizing agent in order to reveal its color. Suitable direct dyes which may be used according to the present invention may be chosen from acidic (anionic), basic (cationic), and neutral dyes.

"Acidic dye" is generally intended to mean a dye containing at least one COOH, $SO_3H$, $PO_3H$, or $PO_4H_2$ group, it being possible for said groups to exist in the form of salts. "Salts" is generally intended to mean salts of metals (for example, alkali metals or alkaline earth metals), salts of an organic amine that is optionally hydroxylated. Such dyes are also referred to as anionic dyes.

The acidic dyes that can be used in the context of this invention can be chosen from acidic nitro dyes, acidic azo dyes, acidic azine dyes, acidic triarylmethane dyes, acidic quinone dyes, acidic indo-amine dyes and acidic natural dyes, and mixtures thereof.

"Basic dyes" is generally intended to mean a dye that has at least one group bearing a positive charge, such as an ammonium group or a quaternized nitrogen atom in a ring. Such dyes are also referred to as cationic dyes.

The basic dyes that can be used in the context of this invention can be chosen from nitrobenzene dyes, azo dyes, azomethine dyes, methine dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylamethane-derived dyes and basic natural dyes, and mixtures thereof.

Preferably, the direct dyes may be present in amounts ranging from 0.001% to 30% by weight, preferably from 0.01% to 20% by weight, more preferably from 0.1% to 10% by weight, based on the total weight of the color base composition.

Representative leuco dyes include those disclosed in US patent application publication no. 20040194231, the entire contents of which is hereby incorporated by reference. Leuco dyes are usually only slightly colored or are not colored at all and can be converted by simple oxidation in air or in the presence of an oxidizing agent into a triheteroylmethane compound. Examples of leuco dyes and corresponding triheteroylmethane compounds include 1H-Benzo[ij]quinolizinium, 9-[bis(2,3,6,7-tetrahydro-1H,5H-benzo[ij]quinolizin-9-yl)methylene]-2,3,5,6,7,9-hexahydro-chloride; 5H-Benzo[a]carbazolium, 11-ethyl-5-[(11-ethyl-11H-benzo[a]carbazol-5-yl)(1-ethyl-1,2,3,4-tetrahydro-5-quinolinyl)methylene]-; Pyrrolo[3,2,1-ij]quinolinium, 8-[bis(1,2,5,6-tetrahydro-4H-pyrrolo[-3,2,1-ij]quinolin-8-yl)methylene]-1,2,4,5,6,8-hexahydro-; Tri(9-ethy-9H-carbazol-3-yl)methane; bis(6-Chloro-9-ethy-9H-carbazol-3-yl)-(9-ethy-9H-carbazol-3-yl)methane; bis(1-(4-sulfo-butyl)-2,3,4,6-tetrahydro-quinolinium)-pyrid-4-yl-methane; bis(1-ethyl-2-methyl-1H-indol-3-yl)-(9-ethy-9H-carbazol-3-yl)methane; Tri(7-ethyl-7H-benzo[c]carbazol-10-yl)methane; bis((6-dimethylamino-3-methyl-1H-indol-2-yl)-2-furylmethane; bis((6-dimethylamino-3-methyl-1H-indol-2-yl)-(pyrid-4-yl)methane; bis(1-ethyl-2-methyl-1H-indol-3-yl)-2-thienyl)methane; 3-[(1-ethyl-2-methyl-1H-indol-3-yl-(9-ethy-9H-carbazol-3-yl) methylene]-1-ethyl-2-methyl-3H-indolium; and 3-[(1-ethyl-2-methyl-1H-indol-3-yl)-2-thienyl)methylene]-1-ethyl-2-methyl-3H-indolium.

Representative optical lightening colorants include those disclosed in US patent application publication no. US20040205905, the entire contents of which is hereby incorporated by reference.

Representative natural colorants include those disclosed in US patent application publication no. US20030159221, the entire contents of which are hereby incorporated by reference. For the purposes of the invention, the expression "natural colorant" means compounds that exist in nature, whether they have been obtained by extraction or reproduced chemically. Examples of natural direct dyes that may be used according to the invention include lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes and especially henna-based poultices or extracts.

2. Developer Composition

The developer composition of the invention is formed from the combination of an anhydrous oxidizer composition containing at least one oxidizing agent and a shampoo composition containing at least one surfactant chosen from anionic, amphoteric, nonionic, zwitterionic, cationic surfactants, and mixtures thereof, and a carrier vehicle.

The at least one oxidizing agent in the anhydrous oxidizer composition employed in this invention is selected from persulfates, perborates, percarbonates, their salts, and mixtures thereof.

Preferred persulfates are monopersulfates, their salts and mixtures thereof such as, for example, potassium persulfate, sodium persulfate, ammonium persulfate, as well as mixtures thereof.

The preferred oxidizing agents in the present invention are potassium persulfate, sodium persulfate and mixtures thereof.

The term "anhydrous" means that the oxidizer composition is either completely free of water or contains no appreciable amount of water, preferably no more than 1% by weight, and more preferably no more than 0.5% by weight, based on the total weight of the anhydrous oxidizer composition.

According to a particularly preferred embodiment of the invention, the anhydrous oxidizer composition is totally anhydrous, that is to say it does not contain any water.

The anhydrous oxidizer composition can contain organic solvents, surfactants, silicones, and mixtures thereof.

Suitable organic solvents include ethanol, isopropyl alcohol, benzyl alcohol, phenyl ethyl alcohol, glycols and glycol ethers, such as ethylene glycol, propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The at least one organic solvent may, for example, be present in an amount ranging from 0.5% to 70% by weight, such as from 2% to 60% by weight, preferably from 5 to 50% by weight, relative to the total weight of the anhydrous oxidizer composition.

The anhydrous oxidizer composition may be in the form of a powder, gel, liquid, foam, lotion, cream, mousse, and emulsion.

In a first preferred embodiment, the oxidizer composition is in powder form.

In a second preferred embodiment, the oxidizer composition is in the form of a gel.

The shampoo composition of the present invention contains at least one surfactant chosen from anionic, amphoteric, nonionic, zwitterionic, cationic surfactants, and mixtures thereof.

The at least one surfactant is preferably present in an amount of from 4% to 50% by weight, more preferably from 6% to 30% by weight, and even more preferably from 8% to 25% by weight, relative to the total weight of the shampoo composition.

Suitable surfactants include:

(i) anionic surfactants such as, for example salts (such as alkaline salts, for example sodium salts, ammonium salts, amine salts, amino alcohol salts, and magnesium salts) of the following compounds: alkyl sulphates, alkyl ether sulphates, alkylamido ether sulphates, alkylaryl polyether sulphates, monoglyceride sulphates, alkyl sulphonates, alkyl Phosphates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl ether phosphates, acyl sarcosinates, acyl isethionates, and N-acyltaurates, wherein the alkyl or acyl radical of all of these various compounds may have from 12 to 20 carbon atoms, and the aryl radical may be chosen from phenyl and benzyl groups. Among the at least one anionic surfactant that may be used, mention may also be made of fatty acid salts such as the salts of oleic, ricinoleic, palmitic, and stearic acids; coconut oil acid; hydrogenated coconut oil acid; and acyl lactylates in which the acyl radical contains 8 to 20 carbon atoms. Use may also be made of at least one weakly anionic surfactant, such as alkyl-D-galactosiduronic acids and their salts, and polyoxyalkylenated carboxylic ether acids and their salts, such as those containing from 2 to 50 ethylene oxide groups. Anionic surfactants of the polyoxyalkylenated carboxylic ether acid or salt type may, for example, correspond to formula (1) below:

$$R_1—OC_2H_4)_n—OCH_2COOA \quad (1)$$

in which:

$R_1$ is chosen from alkyl, alkylamido, and alkaryl groups, and n is chosen from integers and decimal numbers (average value) that may range from 2 to 24, such as from 3 to 10, wherein the alkyl radical has between 6 and 20 carbon atoms approximately, and the aryl radical may be a phenyl;

A is chosen from hydrogen, ammonium, Na, K, Li, Mg, monoethanolamine, and triethanolamine residues. Mixtures of compounds of formula (1) can also be used, for example mixtures in which the groups $R_1$ are different.

Compounds of formula (1) are sold, for example, by the company Chem Y under the name Akypo® (NP40, NP70, OP40, OP80, RLM25, RLM38, RLMQ 38 NV, RLM 45, RLM 45 NV, RLM 100, RLM 100 NV, RO 20, RO 90, RCS 60, RS 60, RS 100, and RO 50) and by the company Sandoz under the name Sandopan® (DTC Acid and DTC).

(ii) nonionic surfactants:

The at least one nonionic surfactant may be chosen from (as a non-limiting list) polyethoxylated, polypropoxylated, and polyglycerolated fatty alcohols; polyethoxylated, polypropoxylated, and polyglycerolated fatty α-diols; polyethoxylated, polypropoxylated, and polyglycerolated fatty alkylphenols; and polyethoxylated, polypropoxylated, and polyglycerolated fatty acids, all having a fatty chain containing, for example, 8 to 18 carbon atoms, it being possible for the number of ethylene oxide or propylene oxide groups to range, for example, from 2 to 50 and for the number of glycerol groups to range, for example, from 2 to 30. Mention may also be made of copolymers of ethylene oxide and of propylene oxide; condensates of ethylene oxide and of propylene oxide with fatty alcohols; polyethoxylated fatty amides, for example polyoethoxylated fatty amides having from 2 to 30 mol of ethylene oxide; polyglycerolated fatty amides having on average 1 to 5, such as 1.5 to 4, glycerol groups; oxyethylenated fatty acid esters of sorbitan having from 2 to 30 mol of ethylene oxide; fatty acid esters of sucrose; fatty acid esters of polyethylene glycol alkylpolyglycosides; N-alkylglucamine derivatives; amine oxides such as $(C_{10}-C_{14})$ alkylamineoxides; and N-acylaminopropylmorpholine oxides. The alkylpolyglycosides may also be mentioned as nonionic surfactants that are suitable in the context of the present disclosure.

(iii) amphoteric or zwitterionic surfactants:

The at least one amphoteric or zwitterionic surfactant can be, for example (as a non-limiting list), aliphatic secondary and tertiary amine derivatives in which the aliphatic radical is a linear or branched chain containing 8 to 18 carbon atoms and containing at least one water-soluble anionic group (for example carboxylate, sulphonate, sulphate, phosphate and phosphonate groups); mention may also be made of $(C_8-C_{20})$ alkylbetaines, sulphobetaines, $(C_8-C_{20})$ alkylamido $(C_1-C_6)$ alkylbetaines, and $(C_8-C_{20})$alkylamido$(C_1-C_6)$alkylsulphobetaines.

Among the amine derivatives, mention may be made of the products sold under the name Miranol®, classified in the CTFA dictionary, 3rd edition, 1982, under the names Amphocarboxyglycinates and Amphocarboxypropionates, which correspond to the respective preferred structures (2) and (3):

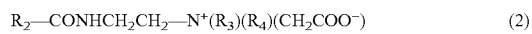

$$R_2—CONHCH_2CH_2—N^+(R_3)(R_4)(CH_2COO^-) \quad (2)$$

in which:

$R_2$ is chosen from alkyl radicals of an acid $R_2$—COOH present in hydrolysed coconut oil, heptyl radicals, nonyl radicals, and undecyl radicals, $R_3$ denotes a β-hydroxyethyl group, $R_4$ denotes a carboxymethyl group;

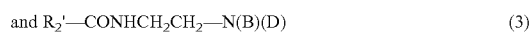

$$\text{and } R_2'—CONHCH_2CH_2—N(B)(D) \quad (3)$$

in which:

B represents —$CH_2CH_2OX'$, D represents —$(CH_2)_z$—Y', wherein z is chosen from 1 and 2, X' is chosen from —$CH_2CH_2$—COOH and hydrogen, Y' is chosen from —COOH and —$CH_2$—CHOH—$SO_3H$, $R_2'$ is chosen from alkyl radicals, such as alkyl radicals of an acid $R_2$—COOH present in coconut oil or in hydrolysed linseed oil; $C_7$, $C_9$, $C_{11}$, $C_{13}$ alkyl radicals, $C_{17}$ alkyl radicals and its iso form; and unsaturated $C_{17}$ radicals.

(iv) cationic surfactants:

The at least one cationic surfactant may be chosen, for example, from: salts of optionally polyoxyalkylenated primary, secondary and tertiary fatty amines; quaternary ammonium salts such as tetra alkyl ammonium, alkylamidoalkyltrialkyl ammonium, trialkylbenzyl ammonium, trialkylhydroxyalkyl ammonium and alkylpyridinium chlorides and bromides; imidazoline derivatives; and cationic amine oxides.

According to a preferred embodiment of the present invention, the shampoo composition comprises at least one surfactant chosen from anionic, amphoteric and zwitterionic surfactants.

The carrier vehicle of the shampoo composition may be any suitable solvent chosen from water, organic solvents, silicones and mixtures thereof.

Prior to use, the anhydrous oxidizer composition and the shampoo composition are combined to form a developer composition.

The developer composition, once formed, will contain the at least one oxidizing agent in an amount ranging from 1% to 80% by weight, preferably from 5% to 75% by weight, more preferably from 6% to 20% by weight, even more preferably from 6% to 10% by weight, based on the total weight of the developer composition.

Moreover, the developer composition can typically have a pH ranging from 3 to 11, such as from 4 to 10, and preferably from 5 to 7.

The developer composition is then applied onto the hair in order to develop color, in situ, to form colored hair.

The developer composition is applied onto the hair for a period of time sufficient to achieve the desired color result. In general, the developer composition is applied onto the hair for a period of from 1 to 20 minutes, such as from 1 to 10 minutes, for example from 1 to 5 minutes.

It should be noted that the use of a catalyst during the oxidation of the oxidative dye precursor such as, for example, cupric or ferrous salt, is not necessary in order to achieve a desired color/shade.

Thus, according to a preferred embodiment of the present invention, both the color base composition and the developer composition of the present invention are substantially free of an oxidation catalyst, i.e., such that the catalyst is present in a less than catalytically effective amount, if at all, in the color base and developer compositions.

As used herein, "oxidation catalyst" refers to transition metal cations that can aid in the oxidation of certain dye precursors, such as cupric and ferrous ions.

According to a particularly preferred embodiment, the color base composition and the developer composition are each totally free of oxidation catalysts.

Similarly, both the color base composition and the developer composition are preferably completely free of hydrogen peroxide ($H_2O_2$).

3. Additional Ingredients

The compositions used in the present invention may also include one or more additional ingredients, which may be incorporated into the color base composition, the anhydrous oxidizer composition, the shampoo composition or in all three compositions. Such ingredients include well-known conventional additives typically employed in hair coloring compositions such as basifying and acidifying agents, buffers, rheological modifiers, conditioning agents, surfactants, antioxidants, fragrances, and chelating agents.

A. Basifying Agents

Basifying (also called alkalizing) and acidifying agents may be used in the compositions of the present invention.

Examples of the basifying or alkalizing agents include ammonia, alcanolamines such as monoethanolamine, diethanolamine, triethanolamine, isopropanolamine, propane-1,3-diamine, oxyethylenated and oxypropylenated hydroxyalkylamines and ethylenediamines, polyamines, sodium hydroxide and potassium hydroxide, ammonium or alkali carbonates, ammonium or alkali bicarbonates, alkali metal carbonates, alkali silicates, alkali metasilicates, organic carbonates, alkali hydroxides, aminomethylpropanol, and mixtures thereof.

The basifying agents may, for example, be present in an amount ranging from 0.05% to 40% by weight, relative to the total weight of each composition.

The basifying agents can in particular be used in the invention to adjust the pH of the shampoo composition and/or the color base composition.

B. Rheological Modifiers

According to the invention, the compositions of the present invention may also comprise at least one rheology modifier chosen from nonionic, anionic, cationic or amphoteric polymers, and other rheology modifiers such as cellulose-based thickeners (hydroxyethylcellulose, hydroxypropylcellulose, carboxymethylcellulose, cationic cellulose ether derivatives, quaternized cellulose derivatives, etc.), guar gum and its derivatives (hydroxypropyl guar, cationic guar derivatives, etc.), gums of microbial origin (xanthan gum, scleroglucan gum, etc.), crosslinked homopolymers of acrylic acid or of acrylamidopropanesulfonic acid and associative polymers as described below.

In particular, the compositions of the present invention may comprise at least one polymer chosen from nonionic, anionic, cationic or amphoteric amphiphilic polymers.

The amphiphilic polymers may contain a hydrophobic chain that is a saturated or unsaturated, aromatic or non-aromatic, linear or branched $C_6$-$C_{30}$ hydrocarbon-based chain, optionally comprising one or more oxyalkylene (oxyethylene and/or oxypropylene) units.

Among the cationic amphiphilic polymers comprising a hydrophobic chain that may be found are cationic polyurethanes or cationic copolymers comprising vinyllactam units and in particular vinylpyrrolidone units.

As examples of nonionic amphiphilic polymers containing a hydrophobic chain, mention may be made, inter alfa, of:

(1) celluloses modified with groups comprising at least one saturated or unsaturated, linear or branched $C_6$-$C_{30}$ hydrocarbon-based chain, for instance hydroxyethylcelluloses modified with groups comprising at least one hydrophobic chain as defined previously, such as especially Natrosol Plus Grade 330 CS ($C_{16}$ alkyls sold by the company Aqualon); Bermocoll EHM 100 (sold by the company Berol Nobel), Amercell Polymer HM-1500 (hydroxyethylcellulose modified with a polyethylene glycol (15) nonylphenyl ether group sold by the company Amerchol);

(2) hydroxypropyl guars modified with groups comprising at least one hydrophobic chain as defined, for example Jaguar XC-95/3 ($C_{14}$ alkyl chain sold by the company Rhodia Chimie); Esaflor HM 22 ($C_{22}$ alkyl chain sold by the company Lamberti); RE210-18 ($C_{14}$ alkyl chain) and RE205-1 ($C_{20}$ alkyl chain) sold by the company Rhodia Chimie;

(3) copolymers of vinylpyrrolidone and of hydrophobic monomers containing a hydrophobic chain as defined above, for instance Antaron or Ganex V216 (vinylpyrrolidone/hexadecene copolymers); Antaron or Ganex V220 (vinylpyrrolidone/eicosene copolymers), sold by the company I.S.P.;

(4) copolymers of $C_1$-$C_6$ alkyl (meth)acrylates and of amphiphilic monomers containing a hydrophobic chain;

(5) copolymers of hydrophilic (meth)acrylates and of hydrophobic monomers comprising at least one hydrophobic chain, for instance the polyethylene glycol methacrylate/lauryl methacrylate copolymer;

(6) polymers with an aminoplast ether skeleton containing at least one fatty chain, such as the Pure Thix compounds sold by the company Sud-Chemie;

(7) linear (block structure), grafted or starburst polyurethane polyethers comprising in their chain at least one hydrophilic block, which is generally a polyoxyethylene block which may comprise between 50 and 1 000 oxyethylene units approximately, and at least one hydrophobic block, which may comprise aliphatic groups alone, optionally combined with cycloaliphatic and/or aromatic blocks. Preferably, the polyurethane polyethers comprise at least two $C_6$-$C_{30}$ hydrocarbon-based hydrophobic chains, separated by a hydrophilic block; the hydrophobic chains may be pendent chains or chains with one or more of the end groups of the hydrophilic block(s).

The polyurethane polyethers comprise a urethane bond between the hydrophilic blocks, but may also contain hydrophilic blocks linked to the lipophilic blocks via other chemical bonds.

Examples of polyurethane polyethers that may be mentioned include Nuvis FX 1100 (European and US INCI name "Steareth-100/PEG-136/HMDI Copolymer" sold by the company Servo Delden); Rheolate 205, 208, 204 or 212 (sold by the company Rheox); Elfacos T210 ($C_{12}$-$C_{14}$ alkyl chain) and Elfacos T212 ($C_{18}$ alkyl chain) sold by the company Akzo.

The anionic amphiphilic polymers containing a hydrophobic chain that may be used comprise, as hydrophobic chain, at least one saturated or unsaturated, aromatic or non-aromatic, linear or branched $C_8$-$C_{30}$ hydrocarbon-based chain.

More particularly, the anionic amphiphilic polymers comprising at least one hydrophobic chain which are crosslinked or non-crosslinked, comprise at least one hydrophilic unit derived from one or more ethylenically unsaturated monomers bearing a carboxylic acid function, or a sulphonic function which is free or partially or totally neutralized, and at least one hydrophobic unit derived from one or more ethylenically unsaturated monomers bearing a hydrophobic side chain, and optionally at least one crosslinking unit derived from one or more polyunsaturated monomers.

The anionic amphiphilic polymers may also comprise at least one sulphonic group, in free or partially or totally neutralized form and at least one hydrophobic portion.

Among these, mention may be made more particularly of acrylamido-2-methyl-2-propanesulphonic (AMPS) acid/n-dodecylacrylamide copolymer neutralized with sodium hydroxide, the copolymer crosslinked with methylenebisacrylamide consisting of 75% by weight of AMPS units neutralized by $NH_3$ and 25% by weight of Genapol T-250 acrylate units, the copolymer crosslinked with allyl methacrylate consisting of 90% by weight of AMPS units neutralized with $NH_3$ and 10% by weight of Genapol T-250 methacrylate units, or the copolymer crosslinked with allyl methacrylate consisting of 80% by weight of AMPS units neutralized with $NH_3$ and 20% by weight of Genapol T-250 methacrylate units.

Other examples include Carbopol ETD-2020 (acrylic acid/$C_{10}$-$C_{30}$ alkyl methacrylate crosslinked copolymer sold by the company Noveon); Carbopol 1382, Pemulen TR1 and Pemulen TR2 (acrylic acid/$C_{10}$-$C_{30}$ alkyl acrylate crosslinked copolymers—sold by the company Noveon), the methacrylic acid/ethyl acrylate/oxyethylenated stearyl methacrylate copolymer (55/35/10); the (meth)acrylic acid/ethyl acrylate/25 EO oxyethylenated behenyl methacrylate copolymer (Aculyn 28 sold by Rohm & Haas) and the methacrylic acid/ethyl acrylate/steareth-10 allyl ether crosslinked copolymer.

When one or more composition(s) of the present invention comprises one or more amphiphilic polymer(s) containing a hydrophobic chain, then this or these polymer(s) generally represent(s) from 0.01% to 20% by weight and preferably, from 0.05% to 10% by weight of the total weight of said composition(s).

The rheology modifier(s) that may be present in the compositions of the present invention can be chosen from polymers of natural origin or synthetic polymers, and are advantageously chosen from those conventionally used in cosmetics.

Examples of synthetic polymers that may be mentioned include polyvinylpyrrolidone, polyacrylic acid, polyacrylamide, non-crosslinked poly(2-acryl-amidopropanesulphonic acid) (Simugel EG from the company SEPPIC), crosslinked poly(2-acrylamido-2-methylpropanesulphonic acid), free or partially neutralized with ammonia (Hostacerin AMPS from Clariant), mixtures of non-crosslinked poly(2-acrylamido-2-methylpropanes-ulphonic acid) with hydroxyalkylcellulose ethers or with poly(ethylene oxide)s, as described in patent U.S. Pat. No. 4,540,510; mixtures of poly((meth)acrylamido ($C_1$-$C_4$)alkylsulphonic acid), which is preferably crosslinked, with a crosslinked copolymer of maleic anhydride and of a ($C_1$-$C_5$)alkyl vinyl ether (Hostacerin AMPS/Stabileze QM from the company ISF).

The thickening polymers of natural origin are preferably polymers comprising at least one sugar unit, for instance nonionic guar gums, optionally modified with $C_1$-$C_6$ hydroxyalkyl groups; biopolysaccharide gums of microbial origin, such as scleroglucan gum or xanthan gum; gums derived from plant exudates, such as gum arabic, ghatti gum, karaya gum, gum tragacanth, carrageenan gum, agar gum and carob gum; pectins; alginates; starches; hydroxy($C_1$-$C_6$)alkylcelluloses and carboxy($C_1$-$C_6$ alkylcelluloses.

It should be noted that the term "sugar unit" denotes a monosaccharide (i.e. monosaccharide or oside or simple sugar) portion, an oligosaccharide portion (short chains formed from a sequence of monosaccharide units, which may be different) or a polysaccharide portion [long chains consisting of monosaccharide units, which may be different, i.e. polyholosides or polyosides]. The saccharide units may also be substituted with alkyl, hydroxyalkyl, alkoxy, acyloxy or carboxyl radicals, the alkyl radicals containing from 1 to 4 carbon atoms.

Examples of nonionic, unmodified guar gums that may be mentioned, inter alia, include Guargel D/15 (Noveon); Vidogum GH 175 (Unipectine), Meypro-Guar 50 and Jaguar C (Meyhall/Rhodia Chimie); and the modified nonionic guar gums that may be mentioned include Jaguar HP8, HP60, HP120, DC 293 and HP 105 (Meyhall/Rhodia Chimie); Galactasol 4H4FD2 (Aqualon).

The biopolysaccharide gums of microbial or plant origin are well known to those skilled in the art and are described especially in the book by Robert L. Davidson entitled "Handbook of Water soluble gums and resins" published by McGraw Hill Book Company (1980).

Among these gums, mention will be made of scleroglucans such as, especially, Actigum CS from Sanofi Bio Industries; Amigel from Alban Muller International, and also the glyoxal-treated scleroglucans described in FR 2 633 940); xanthan gums, for instance Keltrol, Keltrol T, Keltrol Tf, Keltrol Bt, Keltrol Rd, Keltrol Cg (Nutrasweet Kelco), Rhodicare S and Rhodicare H (Rhodia Chimie); starch derivatives, for instance Primogel (Avebe); hydroxyethylcelluloses such as Cellosize QP3L, QP4400H, QP30000H, HEC30000A and Polymer PCG10 (Amerchol), Natrosol 250HHR, 250MR, 250M, 250HHXR, 250HHX, 250HR, HX (Hercules) and Tylose H1000 (Hoechst); hydroxypropylcelluloses, for instance Klucel EF, H, LHF, MF and G (Aqualon); carboxymethylcelluloses, for instance Blanose 7M8/SF, refined 7M, 7LF, 7MF, 9M31F, 12M31XP, 12M31P, 9M31XF, 7H, 7M31, 7H3SXF (Aqualon), Aquasorb A500 (Hercules), Ambergum 1221 (Hercules), Cellogen HP810A, HP6HS9 (Montello) and Primellose (Avebe).

When one or more composition(s) of the present invention comprise one or more rheology modifiers, then this or these rheology modifier(s) generally represent(s) from 0.01% to 20% by weight and better still from 0.05% to 10% by weight of the total weight of said composition(s).

C. Conditioning Agents

The compositions of the present invention may also contain at least one conditioning agent. Such conditioning agents are typically chosen from synthetic oils such as polyolefins, plant oils, fluoro oils or perfluoro oils, natural or synthetic waxes, silicones, non-polysaccharide cationic polymers, compounds of ceramide type, cationic surfactants, fatty amines, fatty acids and derivatives thereof, and also mixtures of these various compounds. Other useful conditioning agents are conditioning polymers which contain primary, secondary, tertiary and/or quaternary amine groups, forming part of the polymer chain or linked directly to the latter, and having a molecular weight of between 500 and approximately 5,000,000, and preferably between 1000 and 3,000,000.

Among these polymers, there may be mentioned, more especially, quaternized proteins, polymers of the polyamine, polyaminoamide or poly(quaternary ammonium) family and cationic polysiloxanes.

The quaternized proteins are, in particular, chemically modified polypeptides bearing quaternary ammonium groups at the end of the chain or grafted onto the latter.

Among the polyamine, polyaminoamide or poly(quaternary ammonium) family of polymers, there may be mentioned:

1) Vinylpyrrolidone/dialkylaminoalkyl acrylate or methacrylate copolymers, quaternized or otherwise, such as the products sold by the company GAF CORPORATION under the name "GAFQUAT", for example "GAFQUAT 734 or 755", or alternatively the products designated "COPOLYMER 845, 958 and 937".

2) The cellulose ether derivatives containing quaternary ammonium groups, especially the polymers marketed by the company UNION CARBIDE CORPORATION under the names "JR" (JR 400, JR 125, JR 30M) or "LR" (LR 400, LR 30M). The polymers are also defined in the CTFA Dictionary as quaternary ammonium derivatives of hydroxyethylcellulose subjected to reaction with an epoxide substituted with a trimethylammonium group.

3) Cationic cellulose derivatives such as cellulose copolymers or cellulose derivatives grafted with a water-soluble quaternary ammonium monomer such as, for example hydroxyalkylcelluloses such as hydroxymethyl-, hydroxyethyl- or hydroxypropylcellulose grafted with a methacryloylethyltrimethylammonium, methacrylamidopropyltrimethylammonium or dimethyldiallylammonium salt.

Marketed products corresponding to this definition are, more especially, the products sold by the company NATIONAL STARCH under the names "CELQUAT L 200" and "CELQUAT H 100".

4) The quaternized polysaccharides marketed under the name "JAGUAR C 13 S", sold by the company MEYHALL.

5) Cyclopolymers having a molecular weight of 20,000 to 3,000,000 such as, for example, the homopolymer of dimethyldiallylammonium chloride sold by the company MERCK under the name "MERQUAT 100", having a molecular weight of less than 100,000, and the copolymer of dimethyldiallylammonium chloride and acrylamide having a molecular weight above 500,000 and sold under the name "MERQUAT 550".

6) Quaternary polymers of vinylpyrrolidone and of vinylimidazole, such as, for example, the products marketed by the company BASF under the names "LUVIQUAT FC 905, FC 550 and FC 370".

Other conditioning polymers which are useable according to the invention are polyalkylenimines, especially polyethylenimines, polymers containing vinylpyridine or vinylpyridinium units, condensates of polyamines and epichlorohydrin, quaternary polyureylenes and chitin derivatives.

Other conditioning polymers which can be incorporated in the compositions of the invention are the cationic polysiloxanes such as those described in U.S. Pat. No. 4,185,087.

The conditioning polymers may also be chosen from amphoteric polymers, such as amphoteric polymers derived from chitosan or copolymers of diallyldialkylammonium and an anionic monomer.

Preferred polymers are, inter alia, polymers containing alkyl groups chosen from groups having 1 to 4 carbon atoms, and more especially methyl and ethyl groups.

Especially preferred conditioning polymers according to the invention are chosen from:
a) the poly(quaternary ammonium) polymers;
b) the copolymer of the diallyldimethylammonium chloride and acrylic acid (80/20) sold by the company CALGON under the name MERQUAT 280;
c) the homopolymer of dimethyldiallylammonium chloride sold by the company MERCK under the name MERQUAT 100;
d) the quaternized cellulose ether derivatives sold by the company UNION CARBIDE under the name JR;
e) the copolymer of vinylpyrrolidone and methacrylamidopropyltrimethylammonium chloride (85:15) sold by the company GAF under the name GAFQUAT HS 100;
f) the polymeric quaternary ammonium salt of acrylamide and beta-methacrylyloxyethyl trimethyl ammonium methosulfate, sold by the company, Nalco, under the names polyquaternium-5 or quaternium-39 or Merquat 5; and
g) the cationic polymers of the ionene type sold by the company Chimex, such as hexadimethrine chloride, also known as IONENE G.

According to a preferred embodiment, the color base composition and/or the developer composition contain at least one conditioning agent as defined above. More preferably, the color base composition and/or the developer composition contain at least one conditioning polymer, in an amount of from 0.01% to 12% by weight, preferably from 0.1 to 10% by weight, more preferably from 0.1 to 8% by weight, all weights being based on the total weight of each composition.

D. Surfactants

The color base composition and/or the anhydrous oxidizer composition may also contain at least one surfactant, chosen from anionic, amphoteric, non-ionic, zwitterionic, and cationic surfactants, and mixtures thereof.

The at least one surfactant may be present in the color base and/or the anhydrous oxidizer composition, in an amount ranging from 0.01% to 40% by weight, such as from 0.05% to 30% by weight, relative to the total weight of each composition.

E. Chelating Agents

One or more composition(s) of the present invention may also contain at least one chelating agent. Preferred ranges of chelating agent are from 0.001% to 5%, preferably from 0.005% to 4%, more preferably from 0.01 to 3% by weight relative to the total weight of each composition. Preferred chelating agents are EDTA, HEDTA, and sodium or potassium salts, and mixtures, thereof.

F. Antioxidants and Reducing Agents

One or more composition(s) of the present invention may also contain at least one antioxidant and/or reducing agent such as ascorbic acid, ascorbylated compounds, such as ascorbyl dipalmitate, t-butylhydroquinone, polyphenols, such as phloroglucinol, thiols, for example, cysteine, sodium sulfite, and sodium hydrosulfite, erythorbic acid, flavonoids, and mixtures thereof. Other examples of reducing agents that are useful include, but are not limited to: anhydrous sodium thiosulfate, powdered sodium metabisulfite, thiourea, ammonium sulfite, thioglycolic acid, thiolactic acid, ammonium thiolactate, glyceryl monothioglycolate, ammonium thioglycolate, thioglycerol, 2,5-dihydroxybenzoic acid, diammonium dithioglycolate, strontium thioglycolate, calcium thiolgycolate, zinc formosulfoxylate, isooctyl thioglycolate, and monoethanolamine thiogylcolate.

The antioxidant and/or reducing agent may be present in an amount ranging from 0.1% to 20% by weight relative to the total weight of each composition.

G. Other Ingredients

The compositions of the present invention can also comprise any additive typically used in cosmetic or hair treatment compositions. The additives may include waxes, organogelators, dispersants, oils, preserving agents, fragrances, fillers, neutralizing agents, hydroxy acids, UV filters, ceramides, pseudoceramides, vegetable, mineral oils, synthetic oils, vitamins, and provitamins.

Needless to say, a person skilled in the art will take care to select the optional additional compound(s) mentioned above such that the advantageous properties intrinsically associated with the compositions of the present invention disclosed herein are not, or are not substantially, adversely affected by the envisaged addition(s).

The present invention relates to a method of coloring hair involving applying the color base composition onto the hair, followed by the application of the developer composition onto the hair, at any time thereafter that is convenient to the consumer from the time of application of the color base composition. According to a preferred embodiment, the developer composition is applied up to 60 minutes after application of the color base composition. The hair being colored may be dry, damp or wet.

It should be noted, however, that in between application of the color base composition and the developer composition, the hair is rinsed in order to remove excess color base composition from the hair. The advantage of employing the rinsing step is that the oxidizing agent is then able to react more thoroughly with the oxidation dye precursor present in and around the hair shaft, thereby achieving enhanced fade resistance and less color loss properties.

Thus, once the color base composition has been applied onto the hair for the desired period of time, the color base composition is rinsed off from the hair. The developer composition is then formed by mixing the anhydrous oxidizer composition with the shampoo composition and applied onto the hair.

Moreover, the oxidation dye precursors in the color are composition are, in general, colorless or weakly colored. When a rinsing step is employed in between application of the color base and developer compositions, the excess oxidation dye precursors are rinsed from the hair and scalp before application of the developer composition. This then allows the hair color to be formed only between the oxidation dye precursors that remain in and on the hair fibers and the oxidizing agent, thereby minimizing, and perhaps even eliminating, the problems of scalp staining and messy applications encountered with conventional hair dyes systems.

The developer composition, once applied, may then be left on the hair for a period of time ranging from 1 to 20 minutes, such as from 1 to 10 minutes, and from 1 to 5 minutes, in order to develop the intended color/shade within and around the hair shaft. The colored hair is then thoroughly rinsed.

The present invention will be better understood from the examples which follow, all of which are intended for illustrative purposes only, and are not meant to unduly limit the scope of the invention in any way.

EXAMPLES

Example 1

The color base composition described hereunder was applied onto individual hair swatches, and allowed to remain in contact therewith for approximately 10 minutes. The hair swatches were then rinsed with water. The developer composition, formed by combining 8 parts by weight of the anhydrous oxidizer composition and 92 parts by weight of the shampoo composition described hereunder, was then applied onto the hair swatches, and the color was allowed to immediately develop in the hair. The developer composition was allowed to remain in contact with the hair for approximately 5 minutes. The hair was then rinsed and dried.

Color Base Composition (pH 9.6)*

| Ingredient | Wt % |
| --- | --- |
| Deionized Water | QS 100% |
| Sodium Hydroxide | pH |
| Pentasodium Pentetate | 2.00 |
| Erythorbic Acid | 0.30 |
| Sodium Metabisulfite | 0.46 |
| N,N-bis(2-hydroxyethyl)-p-phenylenediamine sulfate | 1.00 |
| Cetearyl Alcohol | 7.00 |
| 2,4-diaminophenoxyethanol HCl | 0.80 |
| Fragrance | 1.00 |
| Sclerotium Gum | 0.80 |
| Chlorhexidine Dihydrochloride | 0.05 |
| Methylparaben | 0.30 |
| Amodimethicone (and) Trideceth-6 (and) Cetrimonium Chloride | 1.80 |
| Propylene Glycol | 2.00 |
| Behentrimonium Chloride | 4.00 |
| Cocamidopropyl Betaine | 10.00 |

*note that the pH of the color base composition can be adjusted to various desired levels by monoethanolamine (MEA).

Anhydrous Oxidizer Composition

| Ingredient | Wt % |
| --- | --- |
| Sodium Persulfate | 75.00 |
| Silica | 23.30 |
| Polydecene | 1.70 |

Shampoo Composition

| Ingredient | Wt % |
| --- | --- |
| Ammonium Hydroxide | 3.20 |
| Tartaric Acid | 0.10 |
| Citric Acid | 4.00 |
| Fragrance | 0.50 |
| Polyquaternium-10 | 0.80 |
| Salicylic Acid | 0.45 |
| Benzoic Acid | 0.45 |
| Hexylene Glycol | 1.00 |
| Deionized Water | 65.05 |
| Ethylhexyl Methoxycinnamate | 0.05 |
| Disodium Cocoamphodiacetate | 10.00 |
| PEG-60 Hydrogenated Castor Oil | 0.50 |
| Sodium Laureth Sulfate | 13.85 |
| Tocopheryl Acetate | 0.05 |

Example 2

Salon testing of the inventive compositions of varying shades was conducted by four hair stylists who were experienced with the application and use of commercial permanent and demi-permanent hair color. The stylists were informed that the compositions of the invention could be used for full head applications, for refreshing faded color, toning highlights as well as for lowlights. Each color base composition (identical to the composition described in example 1 above, except for the nature and amounts of the oxidation dye precursors) comprised at least one primary dye intermediate and corresponded to a specific color shade based on the models' previous color treatment and desired result. The shades tested were: medium blonde, dark blonde, medium brown, soft golden brown, blue black, and red shades.

The stylists were each instructed to apply the color base composition of the invention onto the damp or dry hair of 16 models. The color base compositions were allowed to remain in contact therewith for approximately 10 minutes, after which the hair was rinsed with water. The stylists then combined 8 parts by weight of the anhydrous oxidizer composition and 92 parts by weight of the shampoo composition described in example 1 above and applied the resulting developer composition onto the hair of the 16 models. The developer composition was allowed to remain in contact therewith for approximately 5 minutes. The hair was rinsed with water and dried.

Overall, the inventive procedure and compositions were received positively by the stylists in terms of the following properties:
    short processing time of 10 minutes for the color base composition;
    the absence of the smell of ammonia;
    the ease of application of the color base composition onto either damp or dry hair;
    the pigment weight of the tested color;
    ability to even out existing color and toning permanent color or highlights;
    good condition of the hair and allowing for an easy blow-out without using any additional products;
    provided shine and did not weigh the hair down;
    ease of mixing of the anhydrous oxidizer composition and the shampoo composition;
    no stains on the scalp and/or around the hair line.

Example 3

Evaluation of Hair Damage

Hair damage can be evaluated from the surface hydrophobicity/hydrophillicity of hair. The greater the extent of damage to the hair fibers, the lower the degree of hydrophobicity of the hair. In the present example, the hydrophobicity of hair was determined by taking contact angle measurements of water drops deposited on hair fibers.

In this study, the hair fibers were treated:
    either according to the inventive procedure, using the method and compositions as described in example 1 above at two different pH values (9.6 and 6.8) for the color base composition;
    or according to two other conventional hair coloring systems, in which the color base composition and the developer composition are premixed before application onto individual hair swatches, and the mixture is allowed to remain in contact therewith for approximately 20 minutes before rinsing.

The measured contact angles for the hair fibers treated according to the invention were, on average, higher than those measured for the hair treated with the conventional hair coloring systems. The higher the contact angle, the more hydrophobic the hair is. This indicates that damage to the hair fibers treated according to the invention was reduced when compared to the damage to the hair treated with the conventional systems.

The invention claimed is:

1. A method of permanently coloring hair, comprising the steps of
    (a) providing a color base composition containing,
        (iii) at least one primary dye intermediate chosen from ortho-aminophenols, para-aminophenols, oho-phenylenediamines, para-phenylenediamines, double bases, heterocyclic bases, the acid addition salts thereof, and mixtures thereof; and
        (iv) at least 5% by weight of water, based on the total weight of the color base composition, wherein the color base composition has a pH ranging from 2 to 12;
    (b) applying the color base composition onto the hair;
    (c) rinsing the color base composition from the hair;
    (d) providing an anhydrous oxidizer composition containing at least one oxidizing agent chosen from persulfates, perborates, percarbonates, their salts, and mixtures thereof;
    (e) providing a shampoo composition containing a carrier vehicle and at least 4% by weight, based on the total weight of the shampoo composition, of at least one surfactant chosen from anionic, amphoteric, nonionic, zwitterionic, cationic surfactants, and mixtures thereof;
    (f) combining (d) and (e) immediately prior to use, to form a developer composition, wherein the developer composition contains from 1% to 80% by weight of the oxidizing agent, based on the total weight of the developer composition;
    (g) applying the developer composition onto the hair in order to develop color, in situ, to form colored hair; and
    (h) rinsing the developer composition from the hair.

2. The method of claim 1, wherein the color base composition and the developer composition are each substantially free of an oxidation catalyst.

3. The method of claim 1, wherein the at least one oxidizing agent is chosen from perborates, theirs salts and mixtures thereof.

4. The method claim 1, wherein the at least one oxidizing agent is chosen from percarbonates, their salts and mixtures thereof.

5. The method claim 1, wherein the at least one oxidizing agent is chosen from monopersulfates, their salts and mixtures thereof.

6. The method of claim 5, wherein the at least one oxidizing agent is chosen from potassium persulfate, sodium persulfate, ammonium persulfate, and mixtures thereof.

7. The method of claim 1, wherein the at least one oxidizing agent is present in an amount ranging from 5% by weight to 75% by weight, based on the total weight of the developer composition.

8. The method of claim 1, wherein the color base composition does not contain hydrogen peroxide.

9. The method of claim 1, wherein the developer composition does not contain hydrogen peroxide.

10. The method of claim 1, wherein the color base composition has a pH ranging from 2 to 6.9.

11. The method of claim 1, wherein the color base composition has a pH ranging from 7 to 12.

12. The method of claim 1, wherein the pH of the developer composition ranges from 3 to 11.

13. The method of claim 1, wherein the oxidizer composition comprises at least one organic solvent in an amount ranging from 0.5% to 70% by weight, relative to the total weight of the anhydrous oxidizer composition.

14. The method of claim 13, wherein the at least one organic solvent is chosen from ethanol, isopropyl alcohol, benzyl alcohol, phenyl ethyl alcohol, glycols and glycol ethers, such as ethylene glycol, propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

15. The method of claim 1, wherein the shampoo composition comprises the at least one surfactant in an amount of from 4% to 50% by weight, relative to the total weight of the shampoo composition.

16. The method of claim 1, wherein the at least one surfactant is chosen from anionic, amphoteric and zwitterionic surfactants.

17. A kit for coloring a keratinous substrate comprising:
(a) a multi-unit receptacle;
(b) at least one unit comprising a color base composition, the color base composition containing:
　(i) at least one primary dye intermediate chosen from ortho-aminophenols, para-aminophenols, ortho-phenylenediamines, para-phenylenediamines, double bases, heterocyclic bases, the acid addition salts thereof, and mixtures thereof; and
　(ii) at least 5% by weight of water, based on the total weight of the color base composition, wherein the color base composition has a pH ranging from 2 to 12; and
(c) at least one unit comprising an anhydrous oxidizer composition containing at least one oxidizing agent chosen from persulfates, perborates, percarbonates their salts, and mixtures thereof; and
(d) at least one unit comprising a shampoo composition containing a carrier vehicle and at least 4% by weight, based on the total weight of the shampoo composition, of at least one surfactant chosen from anionic, amphoteric, nonionic, zwitterionic, cationic surfactants, and mixtures thereof.

18. The method of claim 2, wherein the at least one oxidizing agent is chosen from perborates, theirs salts and mixtures thereof.

19. The method claim 2, wherein the at least one oxidizing agent is chosen from percarbonates, their salts and mixtures thereof.

20. The method of claim 2, wherein the at least one oxidizing agent is chosen from monopersulfates, their salts and mixtures thereof.

* * * * *